United States Patent [19]

Kagawa et al.

[11] Patent Number: 5,777,007
[45] Date of Patent: Jul. 7, 1998

[54] BROMINATED P-CUMYLPHENOL FLAME-RETARDANTS FOR RESIN COMPOSITION

[75] Inventors: Takumi Kagawa; Norihisa Kondo. both of Shin-Nanyo; Noriyuki Kasai. Tokuyama; Hideo Sakka. Kudamathu. all of Japan

[73] Assignee: Tosoh Corporation. Shinnanyo. Japan

[21] Appl. No.: 814,462

[22] Filed: Mar. 10, 1997

[30] Foreign Application Priority Data

Mar. 13, 1996 [JP] Japan .................... 8-055951

[51] Int. Cl.⁶ .............. C08K 5/136; C07C 39/367; C07C 43/23; C07D 303/14
[52] U.S. Cl. ............. 524/114; 524/109; 524/281; 524/341; 524/369; 524/373; 549/517; 549/559; 567/641; 567/745
[58] Field of Search .................... 568/745, 641; 549/517, 539; 528/102; 525/396; 524/341, 369, 373, 109, 114, 281

[56] References Cited

U.S. PATENT DOCUMENTS

| | | |
|---|---|---|
| 3,277,048 | 10/1966 | Sonnabend .................... 549/559 |
| 3,383,432 | 5/1968 | Krimm et al. .................... 549/517 |
| 3,422,063 | 1/1969 | Barton et al. .................... 549/517 |
| 3,477,990 | 11/1969 | Dante et al. .................... 549/517 |
| 3,723,335 | 3/1973 | Tanaka et al. .................... 549/517 |
| 3,825,522 | 7/1974 | Vargin et al. .................... 549/559 |
| 3,929,908 | 12/1975 | Orlando et al. .................... 549/559 |
| 4,032,510 | 6/1977 | Floyd et al. .................... 524/281 |
| 4,562,216 | 12/1985 | Kishida et al. .................... 524/373 |
| 4,879,329 | 11/1989 | Honpo et al. .................... 524/341 |
| 5,180,525 | 1/1993 | Umeda et al. .................... 524/281 |

FOREIGN PATENT DOCUMENTS

| | | |
|---|---|---|
| 49-103842 | 10/1974 | Japan . |
| 59-142246 | 8/1984 | Japan . |

*Primary Examiner*—Veronica P. Hoke
*Attorney, Agent, or Firm*—Oblon. Spivak. McClelland. Maier & Neustadt. P.C.

[57] ABSTRACT

Brominated p-cumylphenol represented by the formula (1) described hereinafter and derivative thereof represented by the formula (2) described hereinabove. process for the preparation of the same. and flame-retardant resin compositions containing the same. are disclosed. Those compounds are useful flame retardant. and can be blended with various thermosetting resins or thermoplastic resins to obtain flame retardant resin compositions.

15 Claims, No Drawings

BROMINATED P-CUMYLPHENOL FLAME-RETARDANTS FOR RESIN COMPOSITION

FIELD OF THE INVENTION

This invention relates to a novel brominated p-cumylphenol and derivative thereof. These compounds according to the present invention can be used as a flame retardant for blending a flame retardant resin frequently used in various electrical equipments.

BACKGROUND OF THE INVENTION

For the flame retardation of a synthetic resin, a bromine flame retardant, phosphate flame retardant, inorganic flame retardant or the like is conventionally added to various resins and the selection of the flame retardant from these retardants is conducted according to the purpose of use. Representative flame retardants include decabromodiphenyl oxide, tetrabromobisphenol-A (hereinafter affreviated as "TBA"), TBA-epoxy oligomer, magnesium hydroxide and aluminum hydroxide.

As described above, various flame retardants are proposed and they are used appropriately according to the purpose of use. In recent days, however, there is an increasing demand for the reinforcement of regulation on flame retardation and for further improvement in the performance of the flame-retardant resin by the addition of the flame retardant. It is therefore desired to prepare a flame retardant which can supplement disadvantages of the conventional product.

SUMMARY OF THE INVENTION

The present inventors have conducted extensive research on a novel bromine flame retardant and found brominated p-cumylphenols and brominated p-cumylphenol derivatives obtained therefrom. Furthermore, it has been found that the resin to which such a bromine flame retardant has been added has excellent processing properties (fluidity) and it has also been found that the brominated p-cumylphenol derivative according to the present invention has excellent light resistance, leading to the completion of the present invention.

The present invention therefore provides a brominated p-cumylphenol represented by the following formula (1):

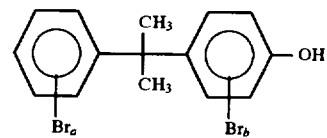

wherein a is an integer of 1 to 3 and b is an integer of 1 to 2;

and a brominated p-cumylphenol derivative represented by the following formula (2):

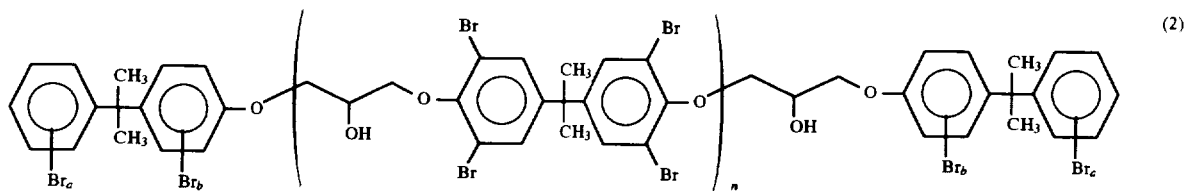

wherein a is an integer of 1 to 3, b is an integer of 1 to 2 and n is an integer of 1 or greater, or the following formula (3):

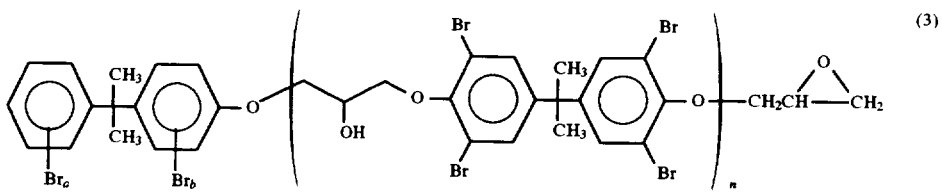

wherein a, b and n have the same meanings as defined above.

The present invention also provides a process for the preparation of the brominated p-cumylphenol or brominated p-cumylphenol derivative.

The present invention further provides a flame retardant resin composition comprising the same.

Brominated p-cumylphenols and brominated p-cumylphenol derivatives according to the present invention are useful flame retardants. When those are incorporated in a thermosetting resin or thermoplastic resin, each of the above brominated p-cumylphenol and brominated p-cumylphenol derivatives can exhibit high flame retardant performance without lowering the mechanical properties of the resin.

The present invention will hereinafter be described more specifically.

DETAILED DESCRIPTION OF THE PREFERRED EMBODIMENTS

The brominated p-cumylphenol according to the present invention has a structure represented by the above formula (1), and the representative physical properties thereof are as follows:

(1) The product is in the slightly yellow viscous form at normal temperature and is in the state of a solution at a temperature of 50° C. or more.

(2) The brominated p-cumylphenol obtained by the bromination reaction has an average bromination number falling within a range of from 2.5 to 4.0 and the bromine content of the product falls within a range of 45 wt % to 62 wt %.

The term "average bromination number" as used herein means an average bromination number per one molecule calculated based on its compositional ratio obtained by the elemental analysis of brominated p-cumylphenol.

(3) The product contains, as a result of the analysis by gas chromatography, a dibromo form in an amount of 0.001 to 30 wt %, a tribromo form in an amount of 30 to 99 wt %, a tetrabromo form in an amount of 1 to 80 wt % and a pentabromo form in an amount of 0.01 to 10 wt %, and preferably a dibromo form in an amount of 0.001 to 30 wt %, a tribromo form in an amount of 30 to 95 wt %, a tetrabromo form in an amount of 1 to 65 wt % and a pentabromo form in an amount of 0.01 to 10 wt %.

A description will next be made of a process for preparing a brominated p-cumylphenol of the present invention.

Examples of the process for preparing the brominated p-cumylphenol of the present invention include a process in which p-cumylphenol as a raw material is dissolved in a solvent inert to the reaction in the presence of a catalyst and then a brominating reagent is added dropwise to the resulting solution to effect the reaction.

Examples of the catalyst usable in the present invention include a Lewis acid catalyst such as aluminum chloride, aluminum bromide, ferric chloride, ferric bromide, titanium tetrachloride, titanium trichloride, antimony pentachloride, antimony trichloride, antimony tribromide, tin chloride and trifluoroborane-etherate complex. Depending on the desired bromination number, an appropriate catalyst is selected from the above-exemplified ones. These catalysts may be used either alone or as mixtures of two or more thereof without any problem.

The catalyst can be added in any amount to the raw material p-cumylphenol provided for the reaction. Described specifically, the amount of the catalyst falls within a range of from 0.001 to 100 mole % per mole of the raw material p-cumylphenol. When the amount is smaller than the above range, retardation of the reaction may occur or deactivation of the catalyst may occur due to the impurities derived from the raw material and solvent. Amounts exceeding the above range are not economical. Therefore, the amount of the catalyst preferably falls within a range of from 0.1 to 40 mole %.

No particular limitation is imposed on the brominating reagent usable in the present invention. Specific examples of it include bromine and bromine chloride, with bromine chloride being preferred. The amount of bromine or bromine chloride added varies according to the average bromination number of the desired brominated p-cumylphenol. In general, the brominating reagent is added within a range of from an equimolar amount to 5 times the mole, based on the desired average bromination number, with a range of from equimolar amount to 1.5 times the mole being preferred. The amount of the brominating reagent used is determined according to the kind of the catalyst used and reaction conditions. A mixing ratio of bromine and chlorine used for the preparation of bromine chloride which is used as a brominating reagent is such that chlorine is used in a molar ratio ranging from 0.5 to 1.0 per mole of bromine. By such a ratio, a decrease in the content of a chlorinated product in the product is intended. Amounts of chlorine not lower than equimolar weight produce a large amount of chlorinated by-products and therefore they are not preferred.

No particular limitation is imposed on the solvent usable in the reaction insofar as it is inert to both the brominating reagent and the catalyst, and also can be subjected to azeotropic distillation with water. Specific examples of the solvent include dichloromethane, dibromomethane, chloroform, bromoform, carbon tetrachloride, 1, 2-dichloroethane and 1,1,2-trichloroethane.

The solvent can be used in any weight ratio to the p-cumylphenol which is a raw material provided for the reaction. When the amount of the solvent is less than 1 time the weight of p-cumylphenol, the viscosity of the reaction mixture becomes high after the completion of the reaction so that such an amount is not preferred. Amounts higher than 100 times the weight are not economical. Accordingly, the amount of the solvent preferably falls within a range of from 2 to 50 times the weight.

The reaction temperature differs depending on the brominating reagent, catalyst and desired average bromination number. When bromine is used, the reaction is generally effected at the temperature range of from 0° to 60° C.; when bromine chloride is used or bromine and bromine chloride are used in combination, the reaction is effected within a range of from −30° to 20° C. There is no particular limitation imposed on the time for the dropwise addition of the brominating reagent insofar as it falls within a range permitting the control of the reaction temperature, because the reaction in the present invention is an exothermic reaction.

Post-treatment may be carried out just after the completion of the addition of the brominating reagent or after aging at a predetermined temperature for 1 to 8 hours.

After the completion of the reaction, excess brominating reagent is removed by adding a reducing agent such as hydrazine or sodium bisulfite and then washing with water whereby a solution containing brominated p-cumylphenol is obtained.

The collection of the brominated p-cumylphenol from the solution is conducted by introducing steam into the solution First, the solvent contained in the solution is distilled off and then low-boiling-point products which are impurities by-produced by the bromination reaction are distilled off After distillation, the organic phase in the form of a solution is separated under heated conditions and then allowed to cool down to room temperature, whereby the brominated p-cumylphenol in the viscous form is collected.

Alternatively, the low-boiling-point products can be removed by thin-film distillation, molecular distillation or the like.

A description will next be made of a brominated p-cumylphenol derivative represented by the above formula (2) or (3) and preparation process thereof.

The brominated p-cumylphenol derivative according to the present invention has a bromine content of 40 to 62%; softening point of 80° to 200° C.; has a 5% weight loss temperature of at least 300° C. as measured by a thermobalance which temperature is an indicator of heat resistance and is superior in light resistance to other commercially available agents.

The brominated p-cumylphenol derivative of the present invention can be obtained by reacting a brominated p-cumylphenol represented by the following formula (1) with a compound having an epoxy group at the molecular end thereof represented by the following formula (4):

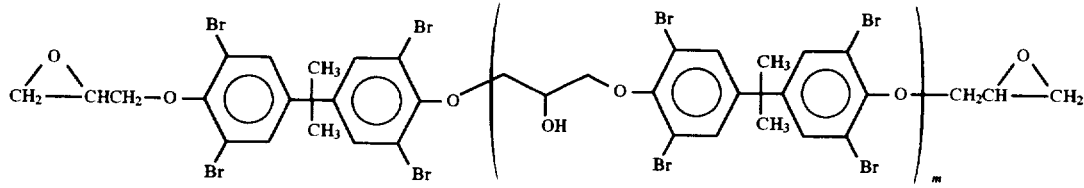

(4)

wherein m is an integer of 0 or greater, in the presence of a catalyst at 80° to 210° C.

The brominated p-cumylphenol, which is used for the preparation of a brominated p-cumylphenol derivative of the present invention, can be used in an amount of 0.5 to 2.0 moles per mole the compound having at its molecular end an epoxy group, with a range of from 0.9 to 2.0 moles being more preferred when the derivative is used for a flame retardant.

Specific examples of the catalyst suitable for use in the preparation of a brominated p-cumylphenol of the present invention includes alkali metal hydroxides such as sodium hydroxide or potassium hydroxide, salts of a quaternary phosphorus compound such as triphenylbenzylphosphonium chloride, triphenylethylphosphonium bromide, butyltriphenylphosphonium chloride, octyltriphenylphosphonium bromide, tetraphenylphosphonium chloride or triphenylmethylphosphonium iodide, and quaternary ammonium salts such as tetramethylammonium chloride, tetramethylammonium bromide, tetraethylammonium chloride, tetraethylammonium bromide, tetra-n-butylammonium chloride, tetra-n-butylammonium bromide, trimethylphenylammonium chloride, trimethylphenylammonium bromide, triethylphenylammonium chloride, triethylphenylammonium bromide, trimethylbenzylammonium chloride and triethylbenzylammonium bromide.

No particular limitation is imposed on the amount of the catalyst, but it is generally added in an amount of 0.01 to 20 mole % based on the brominated p-cumylphenol of the above formula (1).

The reaction temperature differs depending on the kind of the catalyst, but it generally falls within a range of from 80° to 210° C. In the case of a solventless reaction, the reaction is effected under the conditions permitting the melting and stirring of the raw material and product. In the reaction, it is also possible to employ a solvent such as methyl ethyl ketone or methyl isobutyl ketone, or an aromatic hydrocarbon such as toluene, xylene or mesitylene, if required and necessary.

When the reaction is effected in a solventless manner, the desired product is obtained by cooling and solidifying the reaction mixture, followed by pulverization as needed. When the reaction is carried out in a solvent, first the solvent is distilled off and then the desired product is obtained in the same procedure as in the above case.

The brominated p-cumylphenols and brominated p-cumylphenol derivatives according to the present invention can each be used as a flame retardant.

The flame-retardant resin composition according to the present invention comprises a thermosetting resin or thermoplastic resin, brominated p-cumylphenol or brominated p-cumylphenol derivatives of the present invention and a flame retardant assistant. Furthermore, an additive such as ultraviolet absorber, optical stabilizer, antioxidant, antistatic and/or inorganic filler can be added to the composition as needed.

Specific examples of the resin in which the brominated p-cumylphenol or brominated p-cumylphenol derivative of the present invention can be incorporated include thermoplastic resins such as phenol resin, urea resin, melamine resin, unsaturated polyester resin, polyurethane, alkyd resin or epoxy resin; and thermoplastic resins such as low-density polyethylene, high-density polyethylene, ethylene-vinyl acetate copolymer, polystyrene, impact-resistant polystyrene, foamed polystyrene, acrylonitrile-styrene copolymer, acrylonitrilestyrene-butadiene copolymer (hereinafter abbreviated as "ABS"), polypropylene, petroleum resin, polymethyl methacrylate, polyamide, polycarbonate, polyethylene terephthalate, polybutylene terephthalate or polyphenylene ether. In addition, it is also possible to give as examples polymer alloys, such as polycarbonate-ABS or polyphenylene etherpolystyrene, obtained by mixing at least two thermoplastic resins. Of those, thermoplastic resins such as low-density polyethylene, high-density polyethylene, ethylene-vinyl acetate copolymer, polystyrene, impact-resistant polystyrene, foamed polystyrene, acrylonitrile-styrene copolymer, acrylonitrilestyrene-butadiene copolymer (hereinafter abbreviated as "ABS"), polypropylene, petroleum resin, polymethyl methacrylate, polyamide, polycarbonate, polyethylene terephthalate, polybutylene terephthalate or polyphenylene ether are preferred, and polymer alloys, such as polycarbonate-ABS or polyphenylene ether-polystyrene, obtained by mixing at least two thermoplastic resins are also preferred.

The amount of the brominated p-cumylphenol or brominated p-cumylphenol derivative of the present invention added to the resin differs with the kind of the resin or the desired flame retardant performance so that there is no particular limitation imposed on it. In general, however, it is added in an amount of 5 to 50 parts by weight per 100 parts by weight of the resin.

In adding the brominated p-cumylphenol or brominated p-cumylphenol derivative of the present invention to the resin, it is also possible to add a flame retardant assistant such as antimony trioxide or sodium antimonate. In this case, the assistant is generally added in an amount of 5 to 80 parts by weight per 100 parts by weight of brominated polystyrene of the present invention. Furthermore, a benzotriazole ultraviolet absorber, an optical stabilizer such as a 2,2,6,6-tetramethylpiperidine derivative, or a hindered phenol antioxidant may be added as needed. In this case, the additive is generally added in an amount of 0.05 to 5 parts by weight per 100 parts by weight of the flame retardant resin composition of the present invention. In addition, antioxidant or an inorganic filler such as talc or glass fiber may also be added as needed.

As a method of adding the brominated p-cumylphenol or brominated p-cumylphenol derivative of the present invention to the resin, curing may be carried out after dispersing the brominated polystyrene of the present invention in a resin material in advance when a thermosetting resin is employed as the resin material. On the other hand, when a thermoplastic resin is employed, necessary reagents are mixed in a conical blender or tumbler mixer, followed by pelletization with a twin-screw kneader. No particular limitation is imposed on the processing method of a flame retardant resin composition so obtained. For example, the resin composition is subjected to extrusion molding or injection molding, whereby a desired product can be obtained.

The present invention will hereinafter be described more specifically. It should however be understood that the present invention will not be limited to or by the following examples.

EXAMPLE 1

In a 1-liter four necked round flask equipped with a stirrer and a dropping funnel having a cooling jacket, 42.4 g (0.2 mole) of p-cumylphenol, 2.1 g (0.01 mole) of antimony trioxide and 382 g of methylene chloride were charged, followed by cooling to −2° C. using a cooling circulation thermostat.

In a 0.5-liter four necked round flask, 69.9 g (0.44 mole) and 379 g of methylene chloride were charged, followed by cooling to 0° C. using a cooling circulation thermostat. 24.8 g (0.35 mole) of chlorine were blown into the flask over 1 hour to prepare a solution of bromine chloride in methylene chloride. The solution thus obtained was charged in the dropping funnel having a cooling jacket, from which the solution was added dropwise to the p-cumylphenol solution over 6 hours. The resulting solution was then subjected to aging for 30 minutes.

After the completion of the reaction, a 5 wt % hydrazine solution was added to the reaction mixture to remove the remaining bromine chloride and excess bromine, followed by separation and washing with water, whereby a solution of p-cumylphenol was obtained.

Steam was then blown into the brominated p-cumylphenol solution thus obtained to distill off the solvent first and then to distill off the low-boiling-point impurities. After steam distillation, the solution layer of brominated p-cumylphenol was separated while its temperature was maintained. The resulting solution was then dried at 90° C. under reduced pressure, whereby 87.3 g of a brominated p-cumylphenol were obtained in the slightly yellow viscous form. The p-cumylphenol thus obtained was measured for elemental analysis, nuclear magnetic resonance spectrum, gas chromatography and infrared absorption spectrum. The results obtained are shown below.

(1) Elemental analysis

|  | C | H | Br | Cl |
|---|---|---|---|---|
| Found (wt %) | 38.9 | 2.9 | 53.5 | 1.4 |

It has been found that the average bromination number per molecule, which was calculated from the results of the above elemental analysis, was 3.1.

(2) Nuclear magnetic resonance spectrum ($CDCl_3$, H1, ppm):

δ1.4–1.8 (m, 6H), 5.7–5.8 (s, 1H), 6.9–7.6 (m, 5.9H)

(3) Gas chromatography (DB-1, 0.25 mm×15 m):

dibromo form: 0.01 wt %, dibromomonochloro form: 2.27 wt %, tribromo form: 92.49 wt %, tetrabromo form: 4.93 wt %, pentabromo form: 0.01 wt %, low-boiling point products: 0.29 wt %.

(4) Infrared absorption spectrum (KBr, $cm^{-1}$):

3495, 2970, 1763, 1648, 1589, 1559, 1475, 1396, 1364, 1320, 1271, 1246, 1200, 1170, 1141, 1092, 1009, 930, 876, 863, 825, 788, 737, 716.

EXAMPLE 2

In a 1-liter four necked round flask equipped with a stirrer and a dropping funnel having a cooling jacket, 42.4 g (0.2 mole) of p-cumylphenol, 2.1 g (0.01 mole) of antimony trioxide and 382 g of methylene chloride were charged, followed by cooling to −2° C. using a cooling circulation thermostat.

In a 0.5-liter four necked round flask, 89.5 g (0.56 mole) of bromine and 486 g of methylene chloride were charged, followed by cooling to 0° C. using a cooling circulation thermostat. 31.9 g (0.45 mole) of chlorine were blown into the flask over 1 hour to prepare a solution of bromine chloride in methylene chloride. The solution thus obtained was charged in the dropping funnel having a cooling jacket, from which the solution was added dropwise to the p-cumylphenol solution over 12 hours. The resulting mixture was then subjected to aging for 30 minutes.

After the completion of the reaction, a 5 wt % hydrazine solution was added to the reaction mixture to remove the remaining bromine chloride and excess bromine, followed by separation and washing with water, whereby a solution of p-cumylphenol was obtained.

Steam was then blown into the brominated p-cumylphenol solution thus obtained, whereby the solvent and the low-boiling-point impurities were distilled off. After steam distillation, the solution layer of the brominated p-cumylphenol was separated while maintaining the temperature. The resulting solution was then dried at 90° C under reduced pressure, whereby 98.7 g of the brominated p-cumylphenol were obtained in the slightly yellow viscous form. As a result of measurement of the p-cumylphenol thus obtained with gas chromatography, it was found that the brominated p-cumylphenol contained 0.10 wt % of dibromo form, 1.91 wt % of dibromomonochloro form, 17.49 wt % of tribromo form, 77.93 wt % of tetrabromo form, 1.76 w % of pentabromo form and 0.90 wt % of low-boiling point products. As a result of elemental analysis, it was found that the brominated p-cumylphenol had an average bromination number of 3.8.

EXAMPLE 3

To 100 parts by weight of the impact-resistant polystyren (hereinafter abbreviated as "HIPS"; "HT-88", a trade name a product of Mitsubishi Chemical Corp.), 10 parts by weight of the brominated p-cumylphenol obtained in Example 1 an 3.3 parts by weight of antimony trioxide were added, an they were subjected to roll milling at 200° C. After th kneaded mass was press molded at 200° C., a test piece fc evaluation was prepared from the molding. A flammabilit test and measurement of fluidity (MFR: melt flow rate) c the test piece thus obtained were carried out in accordanc with the methods described below.

(1) Flammability test

Flammability of the test piece was evaluated in acco dance with the oxygen index measuring method specified i JIS K 7201 and UL94V vertical flame testing method.

(2) Fluidity (MFR)

The fluidity of the test piece was measured in accordanc with the fluidity (MFR) measuring method (measureme temperature: 200° C., load: 5 kg) specified in JIS K 721 The results obtained are shown in Table 1 below.

EXAMPLES 4 TO 5

A test piece was prepared from the composition shown Table 1 in the same manner as in Example 3. Flammabili and fluidity of each test piece were measured. The results obtained are shown in Table 1 below.

TABLE 1

| Example | Composition to be blended (phr) | | | Flammability test | | |
|---------|------|-------------------------------|-------------------|-------|---------------|------------------|
|         | HIPS | Brominated p-cumyl phenol     | Antimony trioxide | Oxygen Index (OI) | UL94 (1/16B) | Fluidity (MFR) (g/10 min) |
| 3 | 100 | 10 | 3.3  | 12.7 | HB | 20.5 |
| 4 | 100 | 20 | 6.7  | 25.0 | V1 | 38.1 |
| 5 | 100 | 30 | 10.0 | 31.1 | V0 | 69.3 |

Testing apparatus
  Oxygen index:
    "ON-1", trade name; Suga Testing Machine Co., Ltd.
  UL94V flammability test:
    "UL-94V type", trade name; Suga Testing Machine Co., Ltd.
  Fluidity (MFR):
    "T01 system", trade name; Toyo Seiki Seisaku-Sho, Ltd.

COMPARATIVE EXAMPLES 1 TO 3

A test piece was prepared in the same manner as in Example 3 by adding a commercially available TBA ("FG120G", trade name; product of TOSOH Corporation) in an amount shown in Table 2 below to 100 parts by weight of HIPS. Flammability test and measurement of fluidity (MFR) of each test piece were conducted. The results obtained are shown in Table 2 below.

TABLE 2

| Comparative Example | Composition to be blended (phr) | | | Flammability test | | |
|---------|------|-----|-------------------|-------------------|--------------|---------------------------|
|         | HIPS | TBA | Antimony trioxide | Oxygen Index (OI) | UL94 (1/16B) | Fluidity (HFR) (g/10 min) |
| 1 | 100 | 10 | 3.3  | 13.1 | HB | 12.0 |
| 2 | 100 | 20 | 6.7  | 25.5 | V1 | 25.1 |
| 3 | 100 | 30 | 10.0 | 31.6 | V0 | 41.3 |

Testing apparatus
  Oxygen index:
    "ON-1", trade name; Suga Testing Machine Co., Ltd.
  UL94V flammability test:
    "UL-94V type", trade name; Suga Testing Machine Co., Ltd.
  Fluidity (MFR):
    "T01 system", trade name; Toyo Seiki Seisaku-Sho, Ltd.

EXAMPLE 6

In a 1-liter four necked round separable flask equipped with a stirrer, 585.7 g (1.372 mole) of the brominated p-cumylphenol having an average bromination number of 2.61 which had been obtained in the same manner as in Example 1 and 796.6 g (0.70 mole) of tetrabromo bisphenol-A diglycidyl ether ("YDB-400", trade-name; product of Tohto Kasei Co., Ltd., epoxy equivalent: 398.3 g/eq.) were charged, and they were heated on an oil bath to 100° C. for melting.

1.05 g (2.80 mmol) of tetraphenylphosphonium chloride were charged, followed by heating to 160° C. at which the reaction was conducted for 4 hours. The reaction mixture was poured into a metal vat to cool and solidify it, whereby 1,140.6 g of the desired brominated p-cumylphenol derivative were obtained.

The results obtained by conducting or measuring elemental analysis, melting point, epoxy equivalent, nuclear magnetic resonance spectrum, infrared absorption spectrum and thermobalance of the desired product thus obtained are shown below:
(1) Elemental analysis

|              | C    | H   | Br   | Cl  |
|--------------|------|-----|------|-----|
| Found (wt %) | 40.8 | 3.3 | 49.5 | 0.5 |

(2) Melting point: 88°–96° C.
(3) Epoxy equivalent: 30,430 g/eq.
(4) Nuclear magnetic resonance spectrum (CDCl$_3$, H1, ppm):
  δ1.62 (s, 20.7H), 3.58–3.82 (m, 1.9H), 4.13–4.43 (m, 8.7H), 6.97–7.43 (m, 17.7H).
(5) Infrared absorption spectrum (KBr, cm$^{-1}$):
  3559, 2969, 1586, 1537, 1468, 1390, 1270, 1093, 1066, 1008, 933, 873, 825, 740, 659, 573.
(6) Thermal stability (° C.):
  5% weight loss (339), 10% weight loss (353), 50% weight loss (384).

EXAMPLE 7

In a 1-liter four necked round separable flask equipped with a stirrer, 271.9 g (0.63 mole) of the brominated p-cumylphenol having an average bromination number of 2.61 which had been obtained in the same manner as in Example 1 and 1,302.8 g (0.65 mole) of tetrabromo bisphenol-A diglycidyl ether ("YDB-406", Toto Kasei Co., Ltd., epoxy equivalent: 651.4 g/eq.) were charged, and they were heated on an oil bath to 100°C. for melting.

After 0.98 g (2.61 mmol) of tetraphenylphosphonium chloride was charged to the molten mixture, they were heated to 160° C., at which the reaction was carried out for 3 hours. The reaction mixture was poured into a metal vat to cool and solidify it, whereby 1,114.4 g of the desired brominated p-cumylphenol derivative were obtained.

The results obtained by conducting or measuring elemental analysis, melting point, epoxy equivalent, nuclear magnetic resonance spectrum, infrared absorption spectrum and thermobalance of the desired product are shown below.
(1) Elemental analysis

|              | C    | H   | Br   | Cl  |
|--------------|------|-----|------|-----|
| Found (wt %) | 38.9 | 3.1 | 50.3 | 0.2 |

(2) Melting point: 98°–116° C.
(3) Epoxy equivalent: 1,086 g/eq.
(4) Nuclear magnetic resonance spectrum (CDCl$_3$, H1, ppm):
  δ1.61 (s, 18.9H), 2.71–2.78 (m, 1.98), 2.99–3.07 (m, 1.1H), 3.43–3.53 (m, 1.5H), 4.01–4.41 (m, 9.3H), 7.02–7.47 (m, 14.7H).
(5) Infrared absorption spectrum (KBr, cm$^{-1}$):
  3554, 2944, 2368, 1584, 1536, 1411, 1225, 1094, 1065, 1023, 978, 842, 714, 642, 573.
(6) Thermobalance (° C.):
  5% weight loss (309), 10% weight loss (342), 50% weight loss (365).

EXAMPLE 8

To 100 parts by weight of an acrylonitrile-butadiene-styrene copolymer (hereinafter abbreviated as "ABS", "#10", product of Toray Industries, Inc.), 30 parts by weight of the brominated p-cumylphenol derivative obtained in Example 6 and 10 parts by weight of antimony trioxide were added, and they were subjected to roll milling at 210° C. The kneaded mass was press formed at 210° C., whereby a test piece was prepared. The flammability and fluidity (MFR: 220° C., 10 kg/cm$^2$) of the test piece were measured. The results obtained are shown in Table 3 below.

EXAMPLE 9

To 100 parts by weight of ABS, 28 parts by weight of the brominated p-cumylphenol derivative obtained in Example 7 and 9.3 parts by weight of antimony trioxide were added, and a test piece was prepared in the same manner as in Example 8. The flammability and fluidity (MFR at 220° C. and 10 kg/cm$^2$) of the test piece thus obtained were measured. The results obtained are also shown in Table 3 below.

COMPARATIVE EXAMPLE 4

To 100 parts by weight of ABS, 30 parts by weight of a commercially available TBA-epoxy oligomer ("TB-60", trade name; product of Toto Kasei Co., Ltd., the reaction product of TBA-diglycidyl ether and tribromophenol at a molar ratio of 1:2) and 10 parts by weight of antimony trioxide were added, and a test piece was prepared in the same manner as in Example 8. The flammability and fluidity (MFR at 220° C. and 10 kg/cm$^2$) of the test piece thus obtained were measured. The results obtained are shown in Table 3 below.

COMPARATIVE EXAMPLE 5

To 100 parts by weight of ABS, 28 parts by weight of a commercially available TBA-epoxy oligomer ("YDB-408", trade name; product of Toto Kasei Co., Ltd., a TBA-epoxy resin having at its molecular end a glycidyl group) and 9.3 parts by weight of antimony trioxide were added, and a test piece was prepared in the same manner as in Example 8. The flammability and fluidity (MFR at 220° C. and 10 kg/cm$^2$) of the test piece thus obtained were measured. The results obtained are shown in Table 3 below.

TABLE 3

| | Composition to be blended (phr) | | | Flammability test | | |
|---|---|---|---|---|---|---|
| | HIPS | Brominated p-cumyl phenol derivative | Antimony trioxide | Oxygen Index (OI) | UL94 (1/16B) | Fluidity (MFR) (g/10 min) |
| Example 8 | 100 | 30 | 10 | 34.2 | V0 | 62 |
| Example 9 | 100 | 28 | 9.3 | 35.1 | V0 | 51 |
| Comparative Example 4 | 100 | 30 | 10 | 34.2 | V0 | 26 |
| Comparative Example 5 | 100 | 28 | 9.3 | 35.1 | V0 | 44 |

Testing apparatus

Oxygen index:
"ON-1", trade name; Suga Testing Machine Co., Ltd.
UL94V flammability test:
"UL-94V type", trade name; Suga Testing Machine Co., Ltd.
Fluidity (MFR):
"T01 system", trade name; Toyo Seiki Seisaku-Sho, Ltd.

EXAMPLES 10 AND 11 AND COMPARATIVE EXAMPLES 6 AND 7

Concerning each of the test pieces obtained in Example 8, Example 9, Comparative Example 4 and Comparative Example 5, a change in light resistance at 65° C. with the passage of time ($\Delta E$ value as measured by a calorimeter, the value being represented by the following formula:

$$\Delta E \text{ value} = \{(L-L_0)^2 + (a-a_0)^2 + (b-b_0)^2\}^{1/2}$$

$L_0$, $a_0$, $b_0$: value of the test piece measured prior to light resistance test L, a, b: value of the test piece after light resistance test) was measured using I-supper UV-tester (33 mW/cm$^2$).

Results obtained are shown in Table 4 below.

TABLE 4

| | Test piece | Test time of light resistance (hrs) | | | |
|---|---|---|---|---|---|
| | | 0.5 | 1.0 | 2.0 | 3.0 |
| Example 10 | Test piece of Example 8 | 25.8 | 37.0 | 47.8 | 52.4 |
| Example 11 | Test piece of Example 9 | 16.2 | 26.4 | 41.9 | 45.7 |
| Comparative Example 6 | Test piece of Comparative Example 4 | 29.2 | 42.5 | 49.7 | 55.3 |
| Comparative Example 7 | Test piece of Comparative Example 5 | 17.8 | 29.2 | 43.4 | 49.3 |

The brominated p-cumylphenol derivatives obtained in Examples 8 and 9 were superior in light resistance to the commercially available products.

While the invention has been described in detail and with reference to specific embodiments thereof, it will be apparent to one skilled in the art that various changes and modifications can be made therein without departing from the spirit and scope thereof.

What is claimed is:

1. A brominated p-cumylphenol represented by the following formula (1):

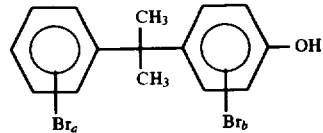

wherein a is an integer of 1 to 3 and b is an integer of 1 to 2.

2. A brominated p-cumylphenol as claimed in claim 1 which has an average bromination number ranging from 2, to 4.0 per one molecule, and comprises 0.001 wt % to 30 w % of dibromo form, 30 wt % to 99 wt % of tribromo form 1 wt % to 80 wt % of tetrabromo form and 0.01 wt % to 1 wt % of pentabromo form.

3. A brominated p-cumylphenol as claimed in claim which comprises 0.001 wt % to 30 wt % of dibromo form 30 wt % to 95 wt % of tribromo form, 1 wt % to 65 wt of tetrabromo form and 0.01 wt % to 10 wt % of pentabrom form.

4. A process for the preparation of a brominate p-cumylphenol as claimed in claim 1, which compris brominating p-cumylphenol with a brominating reagent the presence of a catalyst.

5. A process for the preparation of a brominate p-cumylphenol as claimed in claim 4, wherein the bron nating reagent is bromine chloride.

6. The process as claimed in claim 4, wherein said process is carried out in a solvent and further comprises collecting said brominated p-cumylphenol by distilling off said solvent from said brominated p-cumylphenol, and distilling off a low-boiling point product, which is an impurity by-produced in the brominating reaction, by steam distillation.

7. A flame-retardant resin composition comprising a resin, and the brominated p-cumylphenol as claimed in claim 1, blended therewith.

8. The flame-retardant resin composition according to claim 7, which is obtained by blending 5 to 50 parts by weight of said brominated p-cumylphenol with 100 parts by weight of said resin.

9. A brominated p-cumylphenol derivative represented by the following formula (2):

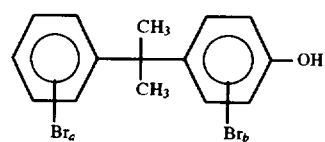

wherein a is an integer of 1 to 3 and b is an integer of 1 to 2.

with an epoxy compound represented by the following formula (4):

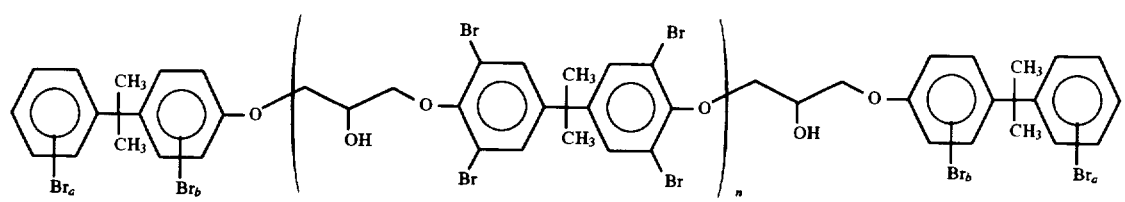

wherein a is an integer of 1 to 3, b is an integer of 1 to 2, and n is an integer of 1 or greater, or by the following formula (3):

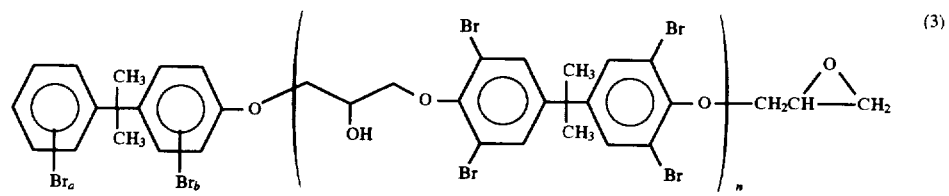

wherein a, b and n have the same as defined above.

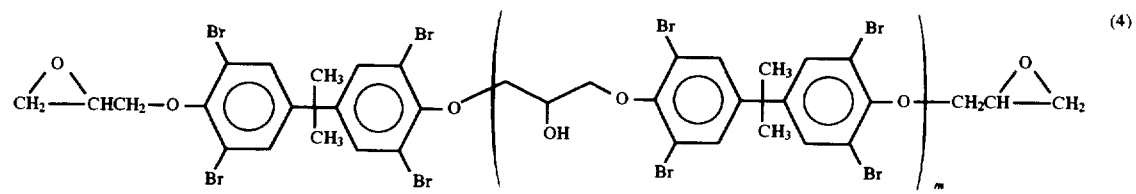

10. A brominated p-cumylphenol derivative, which comprises 0 to 100 mole % of the compound represented by the formula (2) as claimed in claim 9 and 100 to 0 mole % of the compound represented by the formula (3) as claimed in claim 9.

11. A process for the preparation of a brominated p-cumylphenol derivative as claimed in claim 9, which comprises reacting a brominated p-cumylphenol having the following formula (1):

wherein m is an integer of 0 or greater, in the presence of a catalyst.

12. A flame-retardant resin composition comprising a resin and the brominated p-cumylphenol derivative as claimed in claim 9 blended therewith.

13. The flame-retardant resin composition as claimed in claim 12, which is obtained by blending 5 to 50 parts by weight of said brominated p-cumylphenol derivative with 100 parts by weight of said resin.

14. The process as claimed in claim 11, wherein said brominated p-cumylphenol having the formula (1) has an average bromination number ranging from 2.5 to 4.0 per one molecule, and comprises 0.001 wt % to 30 wt % of dibromo form, 30 wt % to 99 wt % of tribromo form, 1 wt % to 80 wt % of tetrabromo form and 0.01 wt % to 10 wt % of pentabromo form.

15. The process as claimed in claim 15, wherein said brominated p-cumylphenol having the formula (1) comprises 0.001 wt % to 30 wt % of dibromo form, 30 wt % to 95 wt % of tribromo form, 1 wt % to 65 wt % of tetrabromo form and 0.01 wt % to 10 wt % of pentabromo form.

* * * * *

UNITED STATES PATENT AND TRADEMARK OFFICE
CERTIFICATE OF CORRECTION

PATENT NO. : 5,777,007
DATED : July 7, 1998
INVENTOR(S) : Takumi KAGAWA, et al.

It is certified that error appears in the above-identified patent and that said Letters Patent is hereby corrected as shown below:

On the title page, item [54] and column 1, "COMPOSITION" should read:

--COMPOSITIONS--

Signed and Sealed this

Twenty-third Day of February, 1999

Attest:

Q. TODD DICKINSON

Attesting Officer

Acting Commissioner of Patents and Trademarks